United States Patent [19]

Ihrman et al.

[11] 4,219,502

[45] Aug. 26, 1980

[54] AROMATIC AMINE ALKYLATION PROCESS

[75] Inventors: Kryn G. Ihrman, Farmington; Manuel Brandt, Huntington Woods, both of Mich.

[73] Assignee: Ethyl Corporation, Richmond, Va.

[21] Appl. No.: 44,671

[22] Filed: Jun. 1, 1979

[51] Int. Cl.$^2$ .............................................. C07C 85/24
[52] U.S. Cl. ................................. 260/578; 260/570 D
[58] Field of Search ........................... 260/578, 570 D

[56] References Cited

U.S. PATENT DOCUMENTS

| | | | |
|---|---|---|---|
| 2,814,646 | 11/1957 | Kolka et al. ........................ | 260/577 |
| 3,275,690 | 9/1966 | Stroh et al. ........................ | 260/576 |
| 3,649,693 | 3/1972 | Napolitano ......................... | 260/578 |
| 3,678,113 | 7/1972 | Klopfer .............................. | 260/578 |
| 3,923,892 | 12/1975 | Klopfer .............................. | 260/578 |

FOREIGN PATENT DOCUMENTS 1148454  4/1969  United Kingdom .................... 260/570

*Primary Examiner*—Robert V. Hines
*Attorney, Agent, or Firm*—Donald L. Johnson; Robert A. Linn; Joseph D. Odenweller

[57] ABSTRACT

An improvement in the process for alkylating the nucleus of an aromatic amine which contains small amounts of a nickel compound by reaction with an olefin in the presence of an aluminum anilide-type catalyst whereby hydrogen sulfide or a sulfide generating compound (e.g. thioacetamide) is added to the aromatic amine to reduce the rate inhibiting effect of the nickel compound.

6 Claims, No Drawings

AROMATIC AMINE ALKYLATION PROCESS

BACKGROUND OF THE INVENTION

Aromatic amines are readily alkylated in a nuclear position by reacting the aromatic amine with an olefin in the presence of an aluminum anilide-type catalyst. Such processes are disclosed at U.S. Pat. Nos. 2,814,646; 3,275,690 and 3,923,892, incorporated herein by reference.

It has been found that the alkylation rate is lowered when the aromatic amine contains certain nickel compounds. Such nickel compounds are sometimes introduced into the aromatic amine when they are made by the nitration of aromatics followed by hydrogenation using a nickel catalyst.

SUMMARY

According to the present invention the alkylation rate of aromatic amines containing nickel cation by reaction with an olefin using an aluminum anilide-type catalyst is enhanced by adding to the aromatic amine prior to alkylation, a small amount of hydrogen sulfide or a compound which reacts with nickel cation to form nickel sulfide.

DESCRIPTION OF THE PREFERRED EMBODIMENTS

A preferred embodiment of the invention is an improvement in the known process for alkylating an aromatic amine in a nuclear position by reaction of the aromatic amine with an olefinic hydrocarbon in the presence of an aluminum anilide-type catalyst, said aromatic amine having an unsubstituted position on a nuclear benzene ring capable of alkylation, said aromatic amine containing a small amount of a nickel compound capable of inhibiting the rate or degree of alkylation. According to the improvement a small amount of a promoter selected from hydrogen sulfide and sulfide generating compounds is added to the aromatic amine prior to conducting the alkylation. The amount of promoter is an amount which is sufficient to reduce the rate-inhibiting effect of the nickel compound.

The alkylation process can be used to alkylate a broad range of aromatic amines as described in the background patents. Illustrative aromatic amines are aniline, p-aminotoluene, o-aminotoluene, 2,4-diaminotoluene, 2,6-diaminotoluene, p-phenylaniline, α-aminonaphthylene, 4,4'-diaminobiphenyl, p-phenylenediamine, 4,4'-methylenebisaniline and the like.

The aluminum anilide-type catalyst is one that contains at least one arylamine group bonded through its nitrogen atom to aluminum. The most common catalyst is aluminum trianilide. These can be formed by reacting aluminum metal or trialkyl aluminum with aniline as described in U.S. Pat. No. 2,814,646. Other similar catalysts can be used in which the anilide group is derived from other aromatic amines such as tolueneamine or toluenediamine.

In other embodiment of the basic process the catalyst is promoted by adding a Friedel-Crafts catalyst to the aluminum anilide catalyzed system. The preferred Friedel-Crafts catalyst is aluminum chloride. This is described in U.S. Pat. No. 3,275,690.

In a still further embodiment of the invention the aluminum anilide-type catalyst is made by adding an alkyl aluminum halide (e.g. diethyl aluminum chloride) to the aromatic amine. This is described in U.S. Pat. No. 3,923,892.

The amount of aluminum anilide-type catalyst should be an amount which gives an aromatic amine:aluminum mole ratio of about 7–25:1, more preferably about 7–15:1.

The olefinic hydrocarbon is preferably a lower monoolefin such as ethylene, propylene, 1-butene, isobutene and the like. The most reactive olefin is ethylene which is highly preferred.

The alkylation is conducted at a temperature high enough to cause the alkylation to proceed, but not so high as to decompose reactants or products. A useful temperature range is about 200°–400° C.

The alkylation is conducted under olefin pressure. A pressure range of about 300–3000 psig can be used. A preferred pressure range is about 500–2000 psig.

The hydrogen sulfide or sulfide generating compound is added to the aromatic amine in an amount sufficient to lower the rate-inhibiting effect of the nickel ion. With toluenediamine containing about 90–100 parts per million (ppm) of nickel ion good results were achieved using about 2–3 millimoles of thioacetamide per mole of toluenediamine. Increased amounts of thioacetamide have a rate-inhibiting effect. The optimum amount to use with any particular aromatic amine can be readily determined by conducting a series of three or four alkylations in which all conditions are maintained constant except using varying amounts of $H_2S$ or sulfide generating compound. A useful range in which to conduct this series of tests is about 1–5 millimoles per mole of aromatic amine. If the results show continued improvement at 5 millimoles the range can be extended upward, for example, to 10 millimoles per mole. Likewise, if the best results are at the lower end the amount used can be reduced.

By "sulfide generating compound" is meant a compound which will react with nickel cation to form nickel sulfide. The preferred promoter is thioacetamide. Other sulfide generating compounds which should give similar results are thiourea, α-mercapto-N-(2-naphthyl acetamide), thioacetanilide, thioacetaldehyde, dithiocarbamate salts or esters such as sodium dithiocarbamate and diethyldithiocarbamate, mercaptans such as butylmercaptan, ammonium sulfide, organic disulfides and trisulfides such as dimethyldisulfide and diisobutyltrisulfide, alkali metal sulfides such as sodium sulfide and polysulfide and the like.

The following example shows the known method of conducting the alkylation of aromatic amines which are substantially nickel-free.

EXAMPLE 1

In this example the aromatic amine was obtained from a commercial grade toluenediamine (TDA) which was made by the nickel-catalyzed hydrogenation of dinitrotoluene. The material was first purified by distillation to obtain an essentially nickel-free TDA distillate.

In an autoclave was placed 329 g of distilled TDA and 33.5 g aniline. The vessel was flushed with nitrogen and then 41 g triethyl aluminum was added. The autoclave was sealed and heated to 150° C. and stirred at that temperature for 20 minutes. It was cooled and vented. After sealing it was heated to 205° C. and pressurized with ethylene to 700 psig. Heating was continued to 300° C. and the ethylene pressure was raised to 1000 psig. The mixture was stirred at 300° C. and the ethylene pressure maintained at 900–1025 psig for 210 minutes.

Samples were taken periodically and analyzed to follow the course of the reaction. The following results were obtained. In the Table "monoethyl" means "monoethylated TDA" and "diethyl" means "diethylated TDA."

Table 1

| Time (min) | Percent Composition | |
|---|---|---|
| | Monoethyl | Diethyl |
| 90 | 3.9 | 80.8 |
| 120 | 2.0 | 82.2 |
| 155 | 1.6 | 81.6 |
| 210 | 1.4 | 79.2 |

These results show that with a nickel-free starting material the reaction is essentially complete by 90 minutes.

The following example shows the results obtained when the distilled TDA is contaminated with a small amount of nickel cation.

EXAMPLE 2

The starting aromatic amine was distilled TDA to which was added nickel carbonate in an amount to provide 100 ppm nickel cation.

In an autoclave was placed 309 gms distilled TDA, 31.4 gms aniline and 0.062 gms nickel carbonate. The vessel was flushed with nitrogen and then 38.4 gms triethyl aluminum was added. The autoclave was heated to 150° C. and stirred at that temperature for 35 minutes. It was cooled and vented. After sealing, it was heated to 200° C. and pressurized with ethylene to 650 psig. Heating was continued to 300° C. and ethylene pressure was raised to 1020 psig. The mixture was stirred for 3 hours at 300° C. under 975–1030 psig ethylene pressure. The final product analyzed:

| TDA | 18.8% |
|---|---|
| Monoethyl TDA | 43.3% |
| Diethyl TDA | 20.2% |

As these results show, the presence of a small amount of nickel cation sharply reduces the alkylation rate and drastically reduces the degree of dialkylation.

The following example shows the results obtained in alkylating a commercial TDA made by the nickel-catalyzed hydrogenation of dinitrotoluene.

EXAMPLE 3

The starting material was a commercial grade TDA containing 95 ppm nickel.

In an autoclave was placed 329 gms TDA and 33.5 gms of aniline. The autoclave was flushed with nitrogen and 41 gms triethyl aluminum was added. The autoclave was sealed and heated to 160° C. It was then cooled and vented. It was again sealed and heated to 265° C. Ethylene feed was started to increase pressure to about 1000 psig at 300° C. Stirring was continued at 300° C. under 1025–1040 psig ethylene for 4 hours. The reaction mixture was periodically sampled and analyzed during the course of the reaction. The following Table shows these results.

Table 2

| Time (min) | Percent Composition | |
|---|---|---|
| | Monoethyl | Diethyl |
| 180 | 21.3 | 58.3 |

Table 2-continued

| Time (min) | Percent Composition | |
|---|---|---|
| | Monoethyl | Diethyl |
| 240 | 18.9 | 61.4 |

These results are similar to those in Example 2, especially in the suppression of diethylation.

The following example shows the effect of a hydrogen sulfide generating compound in lowering the rate-inhibiting effect of nickel cation.

EXAMPLE 4

The aromatic amine used in this example was the same commercial grade TDA containing 95 ppm nickel as used in Example 3.

In a reaction vessel was placed 330 gms TDA and 0.5 gms thioacetamide. This mixture was heated to 110° C. and stirred 30 minutes at that temperature. The product was transferred to an autoclave together with 33.5 gms of aniline. The autoclave was flushed with nitrogen and 41 gms of triethyl aluminum was added. The autoclave was sealed and heated to 150°–160° C. to form the catalyst. It was then cooled and vented. It was again sealed and heated to 150° C. and pressurized to 650 psig with ethylene. The autoclave was heated to 300° C. and maintained at 300° C. under 990–1020 psig ethylene pressure for a total of 4 hours. Samples were withdrawn during the reaction and analyzed. The following results were obtained.

Table 3

| Time (min) | Percent Composition | |
|---|---|---|
| | Monoethyl | Diethyl |
| 150 | 7.5 | 78.7 |
| 210 | 4.4 | 81.0 |
| 240 | 3.3 | 81.4 |

These results show that diethylation was almost 80% complete after 150 minutes. In Example 3, the same TDA but without the thioacetamide was only 61.4% diethylated after 240 minutes under substantially the same reaction conditions. This demonstrates the effect of thioacetamide in promoting both reaction rate and degree of alkylation in the presence of nickel cation.

The alkylated aromatic amines made by this process are useful compounds. For example, diethylated toluenediamine is used as a chain extender in making polyurethane plastic (Br. No. 1,148,454). Alkylated aromatic amines can also be used as antioxidants, dye intermediates and in making pesticides.

We claim:

1. In a process for alkylating an aromatic amine, said aromatic amine having an unsubstituted position on a nuclear benzene ring capable of alkylation, said process comprising reacting an olefinic hydrocarbon with said aromatic amine in the presence of an aluminum anilide-type catalyst, said aromatic amine containing small amounts of a nickel compound capable of inhibiting the rate and/or degree of alkylation, the improvement which comprises adding to said aromatic amine prior to conducting said alkylation a small amount of a promoter selected from the group consisting of hydrogen sulfide and sulfide generating compounds, said small amount of promoter being sufficient to reduce the inhibiting effect of said nickel compound.

2. The process of claim 1 wherein said aromatic amine is toluenediamine.

3. The process of claim 2 wherein said olefinic hydrocarbon is ethylene.

4. The process of claim 1 wherein said promoter is thioacetamide.

5. The process of claim 2 wherein said promoter is thioacetamide.

6. The process of claim 3 wherein said promoter is thioacetamide.

* * * * *